(12) United States Patent
Meskens

(10) Patent No.: US 9,597,522 B2
(45) Date of Patent: Mar. 21, 2017

(54) PORTABLE POWER CHARGING OF IMPLANTABLE MEDICAL DEVICES

(71) Applicant: Werner Meskens, Opwijk (BE)

(72) Inventor: Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/838,666

(22) Filed: Aug. 28, 2015

(65) Prior Publication Data

US 2015/0375003 A1  Dec. 31, 2015

Related U.S. Application Data

(63) Continuation of application No. 12/965,415, filed on Dec. 10, 2010, now Pat. No. 9,132,276.

(51) Int. Cl.
| | |
|---|---|
| *A61N 1/378* | (2006.01) |
| *A61N 1/36* | (2006.01) |
| *H02J 7/02* | (2016.01) |
| *A61N 1/372* | (2006.01) |
| *H02J 17/00* | (2006.01) |

(52) U.S. Cl.
CPC ....... *A61N 1/3787* (2013.01); *A61N 1/36032* (2013.01); *A61N 1/37223* (2013.01); *H02J 7/025* (2013.01); *H02J 17/00* (2013.01); *H04R 2225/31* (2013.01); *H04R 2225/67* (2013.01)

(58) Field of Classification Search
CPC .............. A61N 1/3787; A61N 1/37223; A61N 1/36032; H02J 17/00; H02J 7/025; H04R 2225/31; H04R 2225/67
See application file for complete search history.

(56) References Cited

U.S. PATENT DOCUMENTS

| | | | |
|---|---|---|---|
| 4,532,930 | A  | 8/1985 | Crosby et al. |
| 5,279,292 | A  | 1/1994 | Baumann et al. |
| 5,603,726 | A  | 2/1997 | Schulman et al. |
| 6,275,737 | B1 | 8/2001 | Mann |
| 6,358,281 | B1 | 3/2002 | Berrang et al. |
| 6,658,124 | B1 | 12/2003 | Meadows |
| 7,042,196 | B2 | 5/2006 | Ka-Lai et al. |
| 7,212,110 | B1 | 5/2007 | Martin et al. |

(Continued)

FOREIGN PATENT DOCUMENTS

| | | |
|---|---|---|
| WO | 2008092133    | 7/2008 |
| WO | 2009100981 A1 | 8/2009 |

OTHER PUBLICATIONS

Extended European Search Report in counterpart European Application No. 11846832.1, mailed May 16, 2014, 7 pages.

(Continued)

*Primary Examiner* — Catherine Voorhees
(74) *Attorney, Agent, or Firm* — Edell, Shapiro & Finnan, LLC

(57) ABSTRACT

An implantable medical device, comprising an implantable component having a rechargeable power supply and an external wireless charger. The wireless charger has a rechargeable power supply, and an inductive coil configured to transcutaneously transfer power from the charger power supply to the implantable power supply, and configured to detect and receive, via the inductive coil, power from an auxiliary charger for recharging of the charger power supply.

27 Claims, 9 Drawing Sheets

(56) References Cited

U.S. PATENT DOCUMENTS

| | | |
|---|---|---|
| 7,260,435 B2 | 8/2007 | Ibrahim |
| 7,471,986 B2 | 12/2008 | Hatlestad |
| 2005/0075696 A1 | 4/2005 | Forsberg et al. |
| 2007/0156205 A1 | 7/2007 | Larson et al. |
| 2007/0182367 A1 | 8/2007 | Partovi |
| 2007/0282398 A1 | 12/2007 | Healy et al. |
| 2008/0007217 A1 | 1/2008 | Riley |
| 2008/0228243 A1* | 9/2008 | Maltan ............... A61N 1/36032 607/57 |
| 2008/0300658 A1 | 12/2008 | Meskens |
| 2009/0067653 A1 | 3/2009 | Meskens et al. |
| 2009/0216296 A1 | 8/2009 | Meskens |
| 2010/0046778 A1 | 2/2010 | Crawford et al. |
| 2010/0198303 A1 | 8/2010 | Haller et al. |
| 2011/0193688 A1 | 8/2011 | Forsell |
| 2012/0150259 A1 | 6/2012 | Meskens |

OTHER PUBLICATIONS

International Search Report for International Application No. PCT/IB2011/055590, mailed Sep. 12, 2012, 2 pages.
Office Action in counterpart Japan Application No. 2013-542661, mailed Nov. 24, 2015, 3 pages.

\* cited by examiner

PORTABLE POWER CHARGING OF IMPLANTABLE MEDICAL DEVICES

CROSS-REFERENCE TO RELATED APPLICATIONS

This application is a continuation of U.S. patent application Ser. No. 12/965,415, filed Dec. 10, 2010, the content of which is incorporated herein by reference.

BACKGROUND

Field of the Invention

The present invention relates generally to implantable medical devices, and more particularly, to portable power charging of implantable medical devices.

Related Art

Medical devices having one or more implantable components, generally referred to herein as implantable medical devices, provide a wide range of therapeutic benefits to recipients. Certain implantable medical devices, sometimes referred to as active implantable medical devices (AIMDs), include an implantable power supply that provides power to one or more implantable components. AIMDS include, but are not limited to, certain implantable hearing prostheses, neural stimulators, drug pumps and cardiac devices.

One type of hearing prosthesis that is widely used is the partially implantable cochlear implant. Traditionally, partially implantable cochlear implants consist of an external speech processor unit and an implanted receiver/stimulator unit. The external speech processor unit is worn on the body of the user, such as a behind-the-ear (BTE) device. BTE devices are generally configured to receive sound with a sound input element, such as a microphone, and to convert the received sound into an electrically coded data signal that is transcutaneously transferred to the implanted receiver/stimulator unit. The BTE device is also generally configured to transcutaneously transfer power to the implanted receiver and stimulator unit. More particularly, the power and data are transcutaneously transferred via a magnetic induction link established in a reactive near-field between an external coil closely coupled to an implanted coil.

Traditionally, the operating power for the BTE device and implanted components is provided by batteries, such as Zn-Air batteries, housed in the device. The closely coupled coils include an external coil coupled to the BTE device which is configured to be placed in close proximity to the coil of the implanted component. However, due to improvements in power storage technology, it has become more common for implantable hearing prosthesis and other AIMDs to include an implantable power supply that is sufficient to allow for periods of operation without access to an external power source. Such implantable power storage has enabled certain devices, in particular hearing prostheses, to become totally or fully implantable.

In addition to an implantable power supply, totally implantable hearing prostheses also have one or more components that were traditionally external to the recipient, such as the sound processor, implantable in the recipient. Accordingly, totally implantable prostheses to operate independently (that is, without an external device) for periods of time. It would be appreciated that, as used herein, totally or fully implantable hearing prosthesis may include external devices such as microphones, remote controls, etc.

Various implantable power storage systems have been proposed. However, in all implantable systems it remains necessary to transfer power from an external power supply to recharge the implanted power storage system. Devices continue to use the closely coupled external/internal coils to transfer the power, although the headpiece coil is not continuously required for regular operation. Data transfer may occur using alternative wireless links, for example short range EM (electro-magnetic) links (e.g. 400 MHz) or MI (magnetic induction) links (e.g. 10.7 MHz).

SUMMARY

In one aspect of the present invention, a wireless charger of an implantable medical system is provided. The wireless charger comprises a charger power supply; an inductive coil; and a routing system configured to route power provided by the charger power supply to the inductive coil for transcutaneous transfer of the power to an implantable component, and to route power received via the inductive coil from an auxiliary charger to the charger power supply for recharging of the charger power supply.

In another aspect of the present invention, an implantable medical system is provided. The implantable medical system comprises an auxiliary charger; an implantable component including a implantable power supply; and a wireless charger comprising: a charger power supply, and an inductive coil connected to the charger power supply via a circuit enabling the inductive coil to transcutaneously transfer power from the charger power supply to the implantable power supply and to transfer power received from the auxiliary charger to the charger power supply.

In a still other aspect of the present invention, an implantable medical system is provided. The implantable medical system comprises an external auxiliary charger; and an external wireless charger including: a charger power supply, an inductive coil, and a circuit connected between the charger power supply and the inductive coil configured to drive the inductive coil so as to transmit power an implantable power supply, and configured to detect and receive, via the inductive coil, power from the auxiliary charger for recharging of the charger power supply.

BRIEF DESCRIPTION OF THE DRAWINGS

Embodiments of the present invention are described below with reference to the attached drawings, in which.

DETAILED DESCRIPTION

Figure 1:
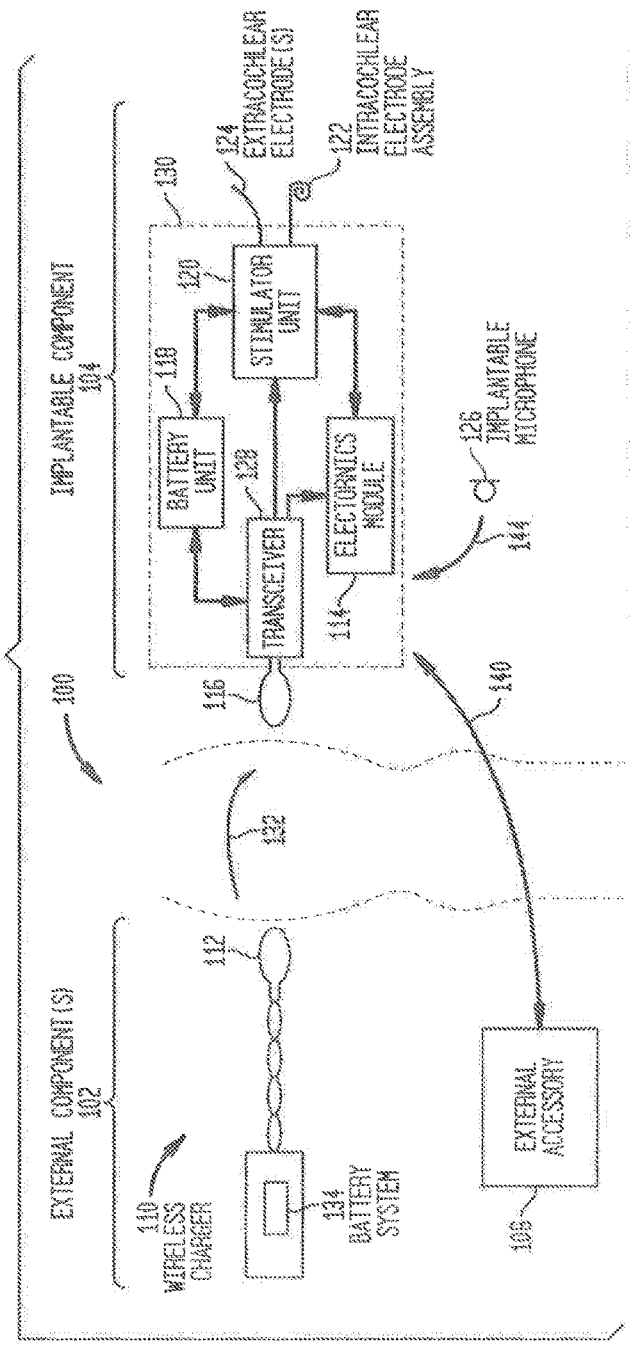
FIG. 1A is a schematic diagram of a cochlear implant, in accordance with embodiments of the present invention.
FIG. 1B is a schematic diagram illustrating exemplary external accessories that may be implemented in accordance with embodiments of the present invention.

Aspects of the present invention are generally directed to an implantable medical device or system having a implantable power supply that receives power from wireless charger worn by a recipient of the device. The wireless charger also includes a rechargeable power supply, and is configured to transcutaneously transfer power to the implantable power supply. The wireless charger is also configured to receive power from an auxiliary charger. In certain embodiments, the wireless charger includes one inductive coil that is used to both receive and transmit power.

Embodiments of the present invention will be described with reference to a particular illustrative implantable medical system, namely a cochlear implant system, commonly referred to as a cochlear prosthesis or simply cochlear implant. It would be appreciated that embodiments of the present invention may be implemented in other medical systems utilizing or requiring periodic transfer of power via an indicative link. Exemplary devices include, but are not limited to, neural or muscle stimulators, drug pumps, cardiac devices, and other hearing prosthesis such as hybrid electrical/acoustic systems, acoustic hearing aid systems, middle ear stimulators, or fully external hearing systems, etc.

FIG. 1A is a schematic diagram of a cochlear implant 100 in accordance with embodiments of the present invention. As shown, cochlear implant 100 comprises an implantable component 104 positioned below a recipient's skin and other tissue (not shown), and external component(s) 102. In the embodiment of FIG. 1A, external component(s) 102 comprise a wireless charger 110, and an external accessory 106. Further details of wireless charger 110 and external accessory 106 are provided below.

As shown, wireless charger 110 includes a radio frequency (RF) headpiece coil 112. Headpiece coil 112 is configured to be inductively coupled to RF coil 116 in implantable component 104 via inductive link 132. Implantable coil 116 is connected to a transceiver unit 128.

As shown, implantable component 104 also includes an implantable power supply, shown as a rechargeable battery unit 118, a stimulator unit 120, an intracochlear electrode assembly 122 and one or more supplementary extracochlear ground electrode(s) 124. In the embodiments of FIG. 1A, transceiver 128, battery unit 118 and stimulator unit 120 are positioned in a hermetically sealed housing 130. Implantable component 104 also includes an electronics module 114 that may comprise, for example, a sound processor, memory, controller, etc.

In the embodiments of FIG. 1A, a separate implantable microphone 126 is also provided. Microphone 126 may be electrically coupled to one or more components in housing 130 via a cable/lead, or via a wireless link 144.

In embodiments of the present invention, wireless charger 110 includes a rechargeable power supply, sometimes referred to herein as charger power supply or battery system 134. In certain embodiments, battery system 134 comprises one or more rechargeable batteries 134. Although for ease of discussion the term battery system is used to refer to the power supply within the charger, it would be appreciated that any rechargeable power source that is able is sufficiently small and is able to fulfill the power requirements of the device may be used. For example, in certain embodiments, a Li-ion or Li-polymer battery unit is used. As is known in the art, such batteries may be shaped to fit perfectly in housings having different geometries. In other embodiments, nickel cadmium, metal hydride, a supercapacitor based system or even energy stored in a spring wound up by a clockwork mechanism may used.

Wireless charger 110 is configured to provide power from battery system 134 to implantable battery unit 118. The power is inductively transferred via link 132. As described further below, battery system 134 of wireless charger 110 is recharged by receiving power from an auxiliary charger via headpiece coil 112.

Figure 9A:
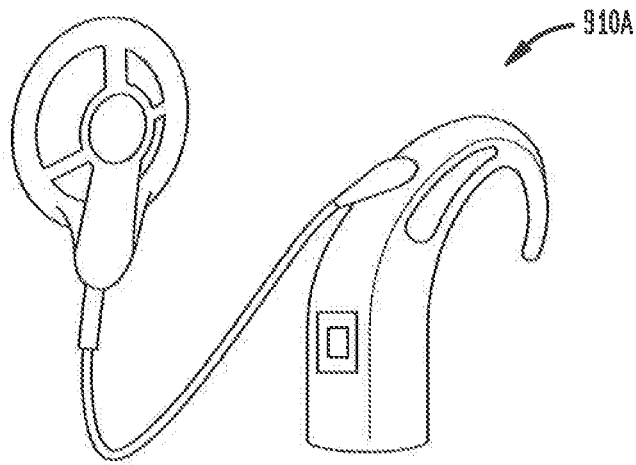
FIG. 9A is a perspective view of a wireless charger, in accordance with embodiments of the present invention.
Figure 9B:
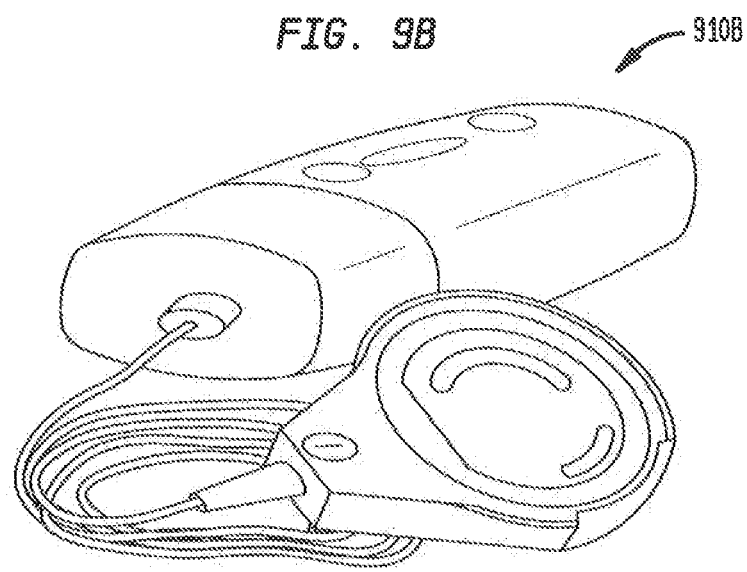
FIG. 9B is a perspective view of a wireless charger, in accordance with embodiments of the present invention.

As previously noted, one or more external accessories 106 may also be worn by the recipient and may communicate with implantable component 104. Specifically, an external accessory 106 is a device that communicates with implantable component 104 via a low-power wireless data link 140. In certain embodiments, an external accessory 106 includes a microphone and/or sound processor. Exemplary external accessories 106 are schematically shown in FIG. 1B as a mini-BTE (106A), micro-BTE (106B), in-the-ear (ITE) device (106C), an in-the canal (ITC) device (106D), open-fit or over-the-ear device (OTE) (not shown), or other device. Exemplary data links are described in US Patent Application US2008/0300658, the contents of which are hereby incorporated by reference herein. FIG. 9A is a perspective view of a wireless charger 910A that is a BTE device. Similarly, FIG. 9B is a perspective view of a body worn charger 910B.

FIG. 1A illustrates embodiments of the present invention in which wireless charger 110 and external accessory 106 are separate components. It would be appreciated that in embodiments of the present invention, external accessory 106 and wireless charger 110 may comprise the same component. For example, in embodiments of the present invention, a BTE device may operate as the wireless charger and may include components of an external accessory, such as a sound processor, microphone etc.

Figure 2:
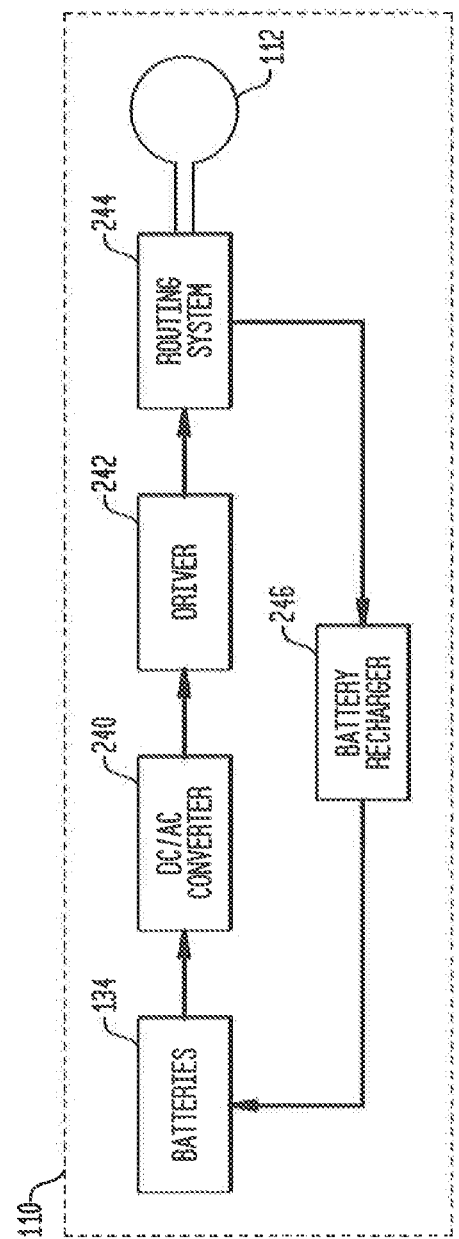
FIG. 2 is a schematic block diagram of a wireless charger, in accordance with embodiments of the present invention.

FIG. 2 is a schematic block diagram of an implementation of a wireless charger 110 of FIG. 1A. As shown, charger 110 includes a power supply, such as rechargeable battery system 134. To transfer power to implantable component 104 (FIG. 1), power from battery system 134 is provided to DC/AC converter 240, that then provides an AC waveform to driver 242. The AC waveform may be modulated for transfer of data to implantable component 104 via link 132 (FIG. 1), or if spreading of the frequency spectrum is desired to reduce dense spectral power components (EMC). Driver 242 amplifies the waveform to a suitable signal level for power transfer to implantable component 104. The amplified signal from driver 242 is provided to routing system 244, which controls the flow of power to and from coil 50. Specifically, routing system 244 is configured to function as a coupler/splitter for signals received from driver 240 and coil 112. Routing system 244 may include components for driving coil 12 to transmit the power signals to implantable component 104.

As previously noted, coil 112 in wireless charger 110 is used to inductively transfer power to implantable component 104, and to receive power from auxiliary charger 350. Using the same coil for both transmission and receipt of power simplifies the manufacturing process and enhances friendliness and simplicity of use. Accordingly, wireless charger 110 receives power from an auxiliary charger via coil 112 and the received power is routed from the coil to battery recharger 246 and battery system 134.

Figure 3:
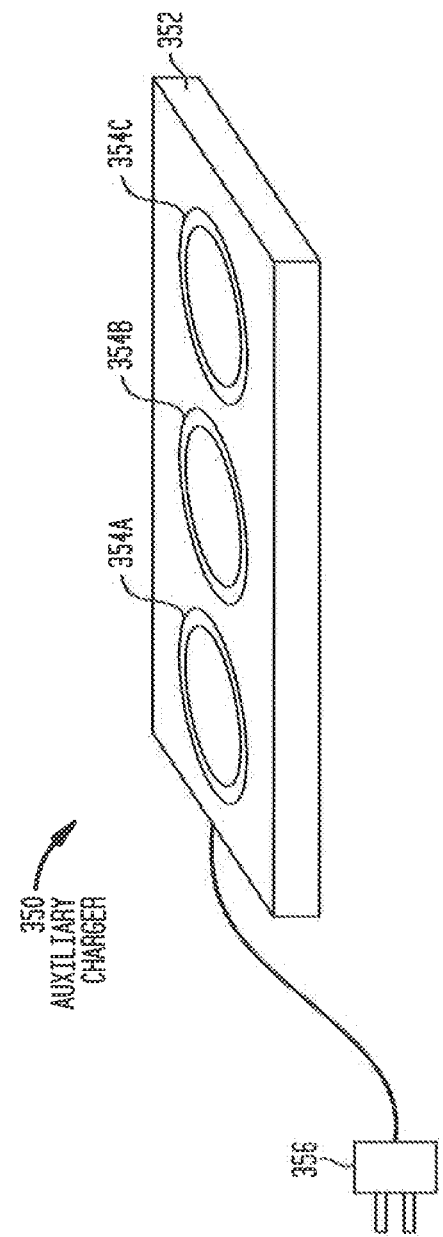
FIG. 3 is a schematic diagram illustrating one implementation of an auxiliary charger, in accordance with embodiments of the present invention.

FIG. 3 is a perspective view of one implementation of an auxiliary charger 350 in accordance with embodiments of the present invention. As shown, auxiliary charger 350 comprises a base 352 on which an array of coils 354A, 354B, and 354C is positioned. Attached to base 356 is a plug 356 for connecting auxiliary charger 350 to a 12V power source, DC power supply (e.g., in a car), or other power sources. In operation, when wireless charger 110 is in proximity to auxiliary charger 350, one of the coils 354A, 354B, or 354C is inductively coupled to coil 112. By having an array of coils 354A-C, rather than only one coil, the system makes it easier for a recipient to couple chargers 110 and 350. Specifically, the array of coils increases the likelihood that the recipient will be able to position the wireless charger 110 appropriately so that an inductive link is formed between coil 112 and a coil 354. When wireless charger 110 is fully charged, auxiliary charger 350 and the wireless charger may be separated.

It would be appreciated that auxiliary charger 350 may have a variety of arrangements. For example, auxiliary charger 350 may be a charging pad, a cradle, a docking station, or any suitable arrangement. Auxiliary charger 350 may also be adapted to charge other devices, for example any externally worn microphone or remote control units.

Figure 4:
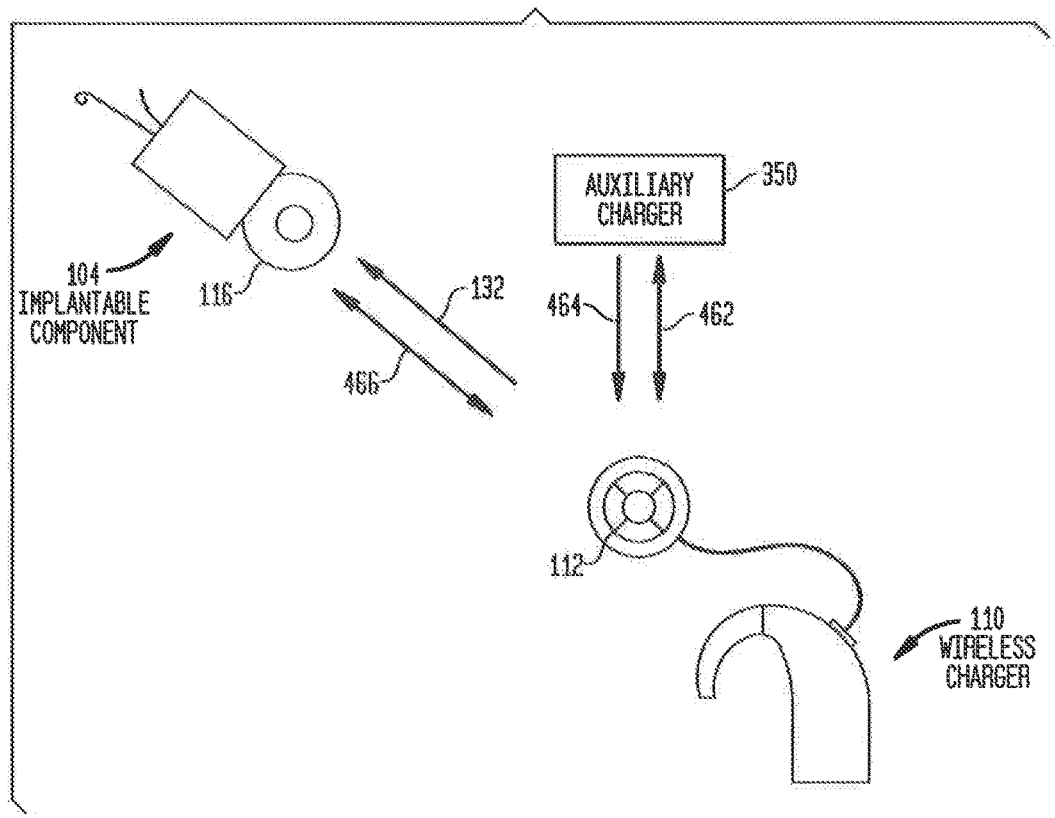
FIG. 4 is a schematic diagram illustrating of a cochlear implant system, in accordance with embodiments of the present invention.

FIG. 4 is a schematic diagram illustrating wireless links between auxiliary charger 350, wireless charger 110 and implantable component 104. As would be appreciated, the links shown in FIG. 4 are merely illustrative and additional links could be provided. Alternatively, all of the links shown in FIG. 4 are not necessary and one or more links may be omitted in different configurations.

As shown in FIG. 4, a wireless power link 464 is provided between a coil 354 (FIG. 3) in auxiliary charger 350, and headpiece coil 112. Additionally, a feedback link 462 is provided to transmit data information between auxiliary charger 352 and wireless charger 110. For example, link 462 may used by wireless charger 110 to instruct auxiliary charger 350 to adjust link 464, or to adjust other characteristics of the auxiliary charger.

Also as shown in FIG. 4, link 132 is provided between implantable coil 116 and headpiece coil 112 to transmit power from wireless charger 110 to implantable component 104. In certain embodiments, a bidirectional data link 466 may also be provided between coils 112 and 116 to transmit data to or from implantable component 104.

As noted above, in embodiments of the present invention a wireless charger also operates as an external accessory. That is, the wireless charger includes components of an external accessory, such as a sound processor, microphone, control electronics, etc. In such embodiments, an additional data link may be provided between the wireless charger and the implantable component. However, in certain embodiments, the wireless charger is a simple charging arrangement that does not otherwise interact with the implantable component.

Figure 5:
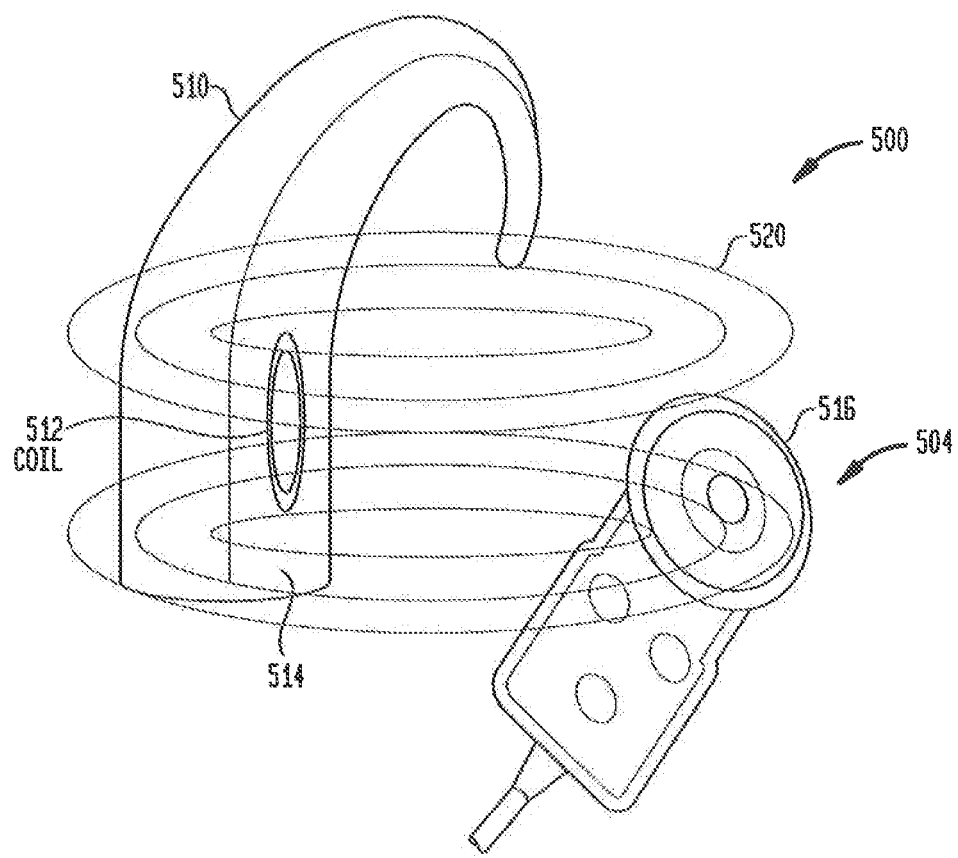
FIG. 5 is a schematic diagram of a wireless charger having the coil integrated in its housing, in accordance with embodiments of the present invention.

FIG. 5 is a schematic diagram of an alternative cochlear implant 500 in accordance with embodiments of the present invention. As shown, cochlear implant 500 comprises an implantable component 504 that is substantially the same as implantable component 104 of FIG. 1. Cochlear implant 500 further comprises a wireless charger 510. As shown, wireless charger 510 has a coil 512 wireless charger in its housing 514.

Also shown in FIG. 5 are exemplary magnetic flux lines 520 generated by coil. As shown, magnetic flux lines 520 pass through implantable coil 516, thereby inductively coupling coil 512 to coil 516.

Figure 6:
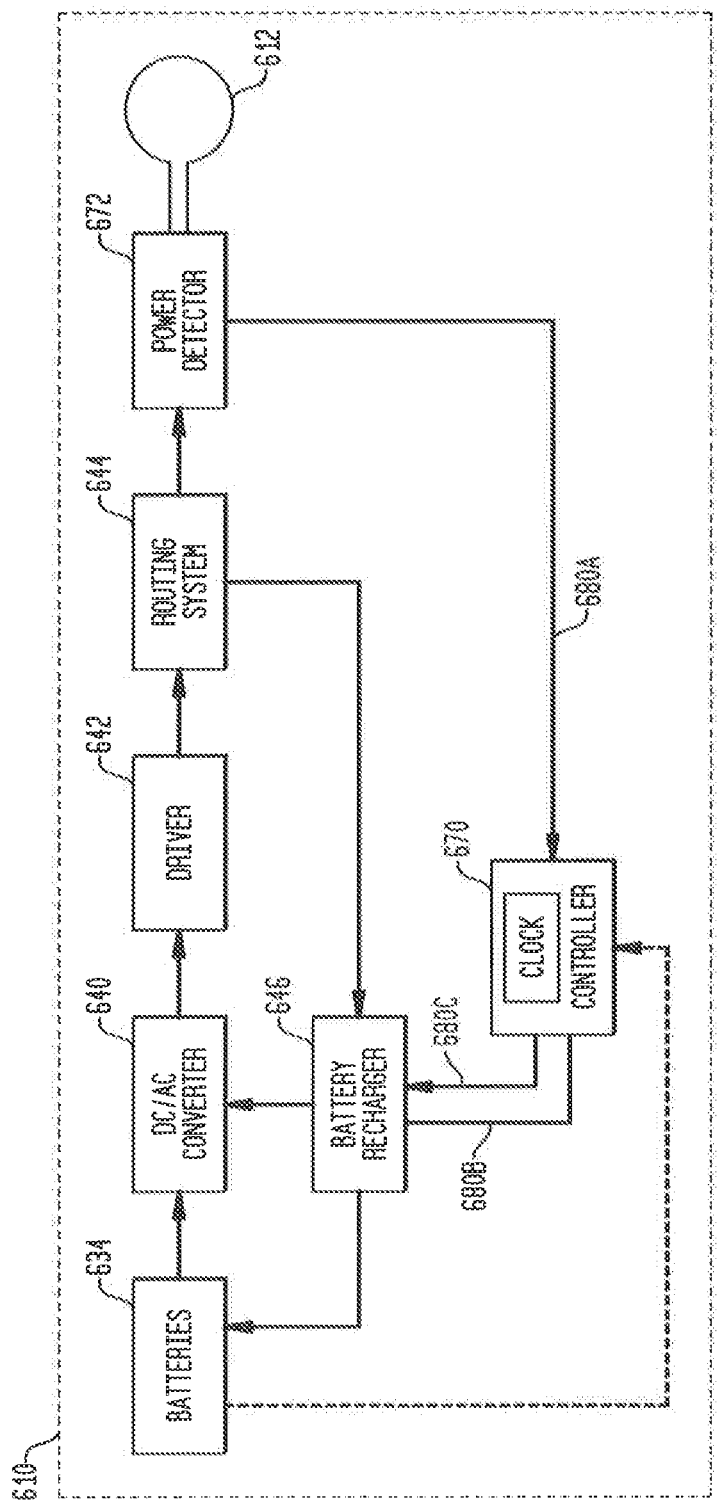
FIG. 6 is a block diagram of an alternative implementation of a wireless charger, in accordance with embodiments of the present invention.
Figure 7:
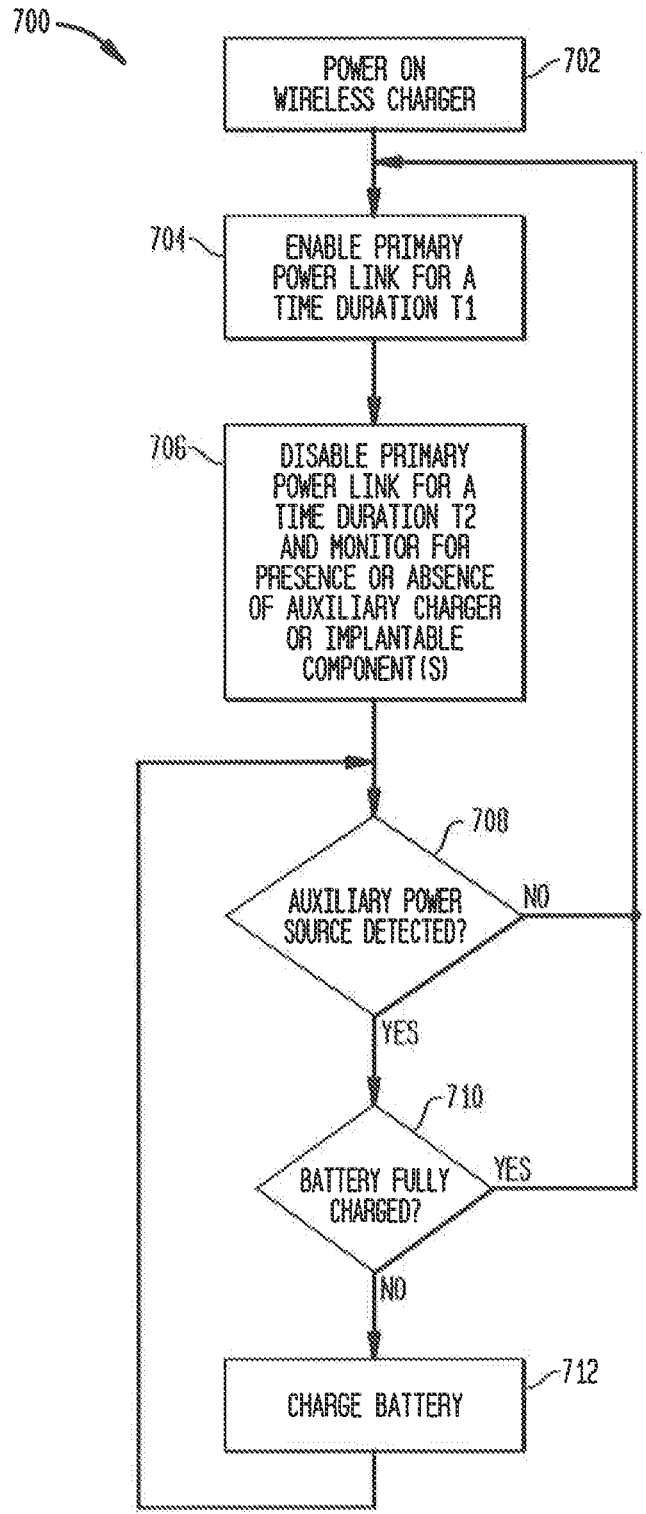
FIG. 7 is a flow chart of a charging process for a wireless charger, in accordance with embodiments of the present invention.

As noted above, FIG. 3 is a schematic block diagram of one embodiment of wireless charger 110 of FIG. 1. FIG. 6 is a schematic block diagram of an alternative wireless charger 610 having a controller 670 to manage recharging and communications of the charger. Charger 610 has components that are substantially the same as described above with reference to FIG. 3, including batteries 634, DC/AC converter 640, driver 642, routing system 644, and battery recharger 646. However, as shown in FIG. 7, wireless charger 610 includes several components, namely power detector 672 and controller 670, that are not found in wireless charger 110 of FIG. 3. As described below, the power emanating from wireless charger unit 610 is provided to the implantable component 104. The auxiliary power emanating from auxiliary charger 350 (FIG. 3) is provided to wireless charger unit 610 to charge the batteries therein or thereon.

For ease of description, the operation of controller 670 will described with reference to the control process 700 of FIG. 7.

Control process begins at block 704 after the wireless charger is powered ON at block 702. More particularly, at block 704 controller 670 of wireless charger 610 initially operates the primary power link for a time duration T1. The primary power link is the link between external coil 612 of wireless charger 610 and the implantable coil. At block 706, controller 670 disables primary power link for a time duration T2, and monitors for the presence of the auxiliary charger. In certain embodiments, T2 is preferably relatively short when compared to T1. Referring to the embodiments of FIG. 6, the presence of the auxiliary charger may be detected by power detector 672. It should be noted that in certain embodiments the primary power link is disabled for a short time at block 706 to allow detection (presence or absence) of auxiliary power sources or implantable components.

At block 708, controller 670 performs a check to determine if the auxiliary charger is detected. If the auxiliary charger is not detected, control process 700 returns to block 704 where controller 670 again enables primary power link for T1. This process continues until the auxiliary charger has been detected.

When the auxiliary power source is detected, control process 700 continues to block 710 where controller 670 performs a check of whether the battery is fully charged. If the battery is not fully charged, controller 670 activates the auxiliary link (that is, the link between the wireless charger and the auxiliary charger), and the battery(ies) of the wireless charger are recharged at block 712. If, at block 710, it is determined that the battery(ies) are fully charged, control process 700 returns to block 704. It would be appreciated that control process 700 of FIG. 7 is one implementation, and other methods for managing wireless charger and the dual purpose coil and associated systems may be implemented in alternative embodiments of the present invention.

Figure 8:
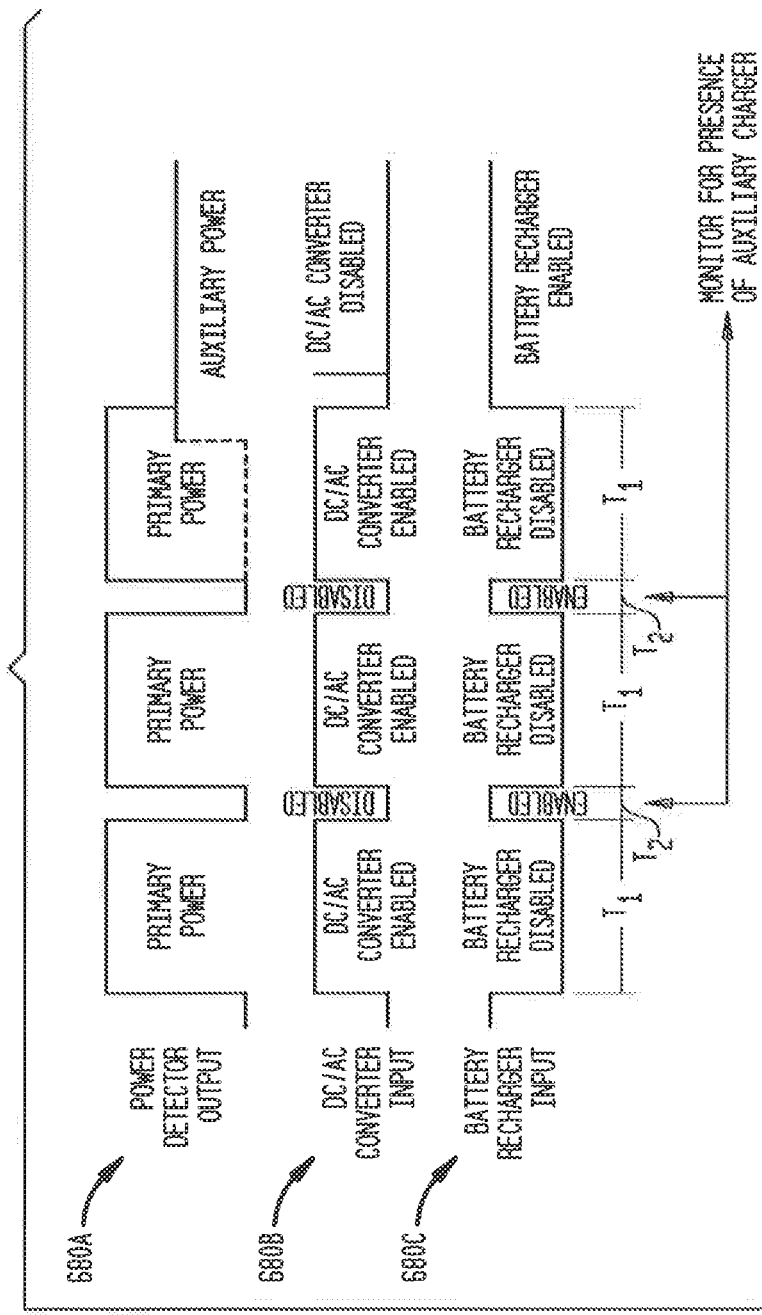
FIG. 8 is a timing diagram corresponding to the method illustrated in FIG. 7.

FIG. 8 is a timing diagram schematically illustrating how certain components of wireless charger 610 are operated during control process 700.

Specifically, FIG. 8 shows the output 680A of power detector 672, the input 680B of DC/AC converter 640, and the output 680C of battery recharger 646 during times T1 and T2. As shown, when power is being provided via the primary link, input 680B of DC/AC converter 640 is high, while output 680C of battery recharger 646 is low (that is, battery recharger 646 is disabled). As noted above, controller 670 monitors for the presence of the auxiliary charger during times T2.

In one embodiment shown in FIG. 4 a wireless backlink 466 from the implantable component 104 to the wireless charger 110, for example similar to the telemetry systems known for cochlear implants, provides the type of implantable component and status information on the state of the implanted rechargeable battery to the recharger during its charging and discharging cycle. The wireless back link is optional and could be operating over the same or a different RF frequency channel. In case the RF frequency channel is shared a TDMA scheme becomes necessary. In both cases the system requires additional communication blocks. As an alternative to TDMA load modulation could be applied by switching on and off a small load resistance on the BTE charger. This would result in a voltage variation over the auxiliary coil such as in amplitude modulation.

All references referred to in the specification are hereby incorporated by reference into this disclosure. Many variations and additions are possible within the general inventive scope.

What is claimed is:

1. A wireless charger of an implantable medical system, comprising:
   a charger power supply;
   an inductive coil;
   a circuit configured to route power provided by the charger power supply to the inductive coil for transcutaneous transfer of the power to an implantable component, and to route power received via the inductive coil from an auxiliary charger to the charger power supply for recharging of the charger power supply; and
   wherein the wireless charger is configured to detect the presence of an inductive field generated by the auxiliary charger, and wherein in response to detection of the presence of the inductive field generated by the auxiliary charger, the circuit is automatically arranged to route power from the inductive coil to the charger power supply.

2. The wireless charger of claim 1, wherein the circuit comprises a routing system, driver and a battery recharger, and wherein the routing system is connected among the driver, the inductive coil, and the battery recharger.

3. The wireless charger of claim 1, further comprising a sound processor, wherein the wireless charger is further configured to transcutaneously transmit data from the sound processor to the implantable component via the inductive coil.

4. The wireless charger of claim 1, further comprising a power detector connected to the inductive coil, wherein the power detector is configured to detect the presence of the inductive field generated by the auxiliary charger.

5. The wireless charger of claim 1, further comprising a controller configured to control the circuit so as to enable routing of power from the charger power supply to the inductive coil only during specified time periods.

6. The wireless charger of claim 1, wherein the wireless charger is a Behind-the-Ear (BTE) device.

7. The wireless charger of claim 1, wherein the wireless charger is a body worn device.

8. An implantable medical system, comprising:
   an implantable component including a implantable power supply; and
   a wireless charger comprising:
      a charger power supply, and
      an inductive coil connected to the charger power supply via a circuit enabling the inductive coil to transcutaneously transfer power from the charger power supply to the implantable power supply and to transfer power received from an auxiliary charger to the charger power supply,
   wherein the circuit is configured to drive the inductive coil with power received from the rechargeable power supply, and to route power received at the inductive coil to the charger power supply.

9. The implantable medical system of claim 8, wherein the circuit comprises a routing system, a driver, and a battery recharger, wherein the routing system is connected among the driver, the inductive coil, and the battery recharger.

10. The implantable medical system of claim 8, wherein the wireless charger further comprises a sound processor, and wherein the inductive coil is further configured to transcutaneously transmit data from the sound processor to the implantable component.

11. The implantable medical system of claim 8, further comprising an external accessory, wherein the inductive coil is configured to form a bidirectional data link with the external accessory.

12. The implantable medical system of claim 8, wherein the circuit includes a controller configured to enable the transcutaneously transfer of power from the charger power supply to the implantable power supply via the inductive coil for a first time period, and to disable the transcutaneously transfer of power from the charger power supply to the implantable power supply via the inductive coil for a second time period.

13. The implantable medical system of claim 12, wherein the circuit is configured to monitor for the presence of the auxiliary charger during the second time period.

14. The implantable medical system of claim 13, wherein when the circuit detects the presence of the auxiliary charger, the inductive coil is configured to receive power from the auxiliary charger and the circuit is configured to enable the transfer of power received from the auxiliary charger to the charger power supply.

15. The implantable medical system of claim 14, wherein before enabling the transfer of power received from the auxiliary charger to the charger power supply, the circuit is configured to perform a check to determine if the charger power supply can accept additional power.

16. The implantable medical system of claim 8, wherein the implantable medical system is a cochlear implant system.

17. An implantable medical system, comprising:
   an external wireless charger including:
      a charger power supply,
      an inductive coil, and
      a circuit connected between the charger power supply and the inductive coil configured to drive the inductive coil so as to transmit power to an implantable power supply, and configured to detect and receive, via the inductive coil, power from an auxiliary charger for recharging of the charger power supply,
   wherein the circuit includes a controller configured to enable the transcutaneous transfer of power from the charger power supply to the implantable power supply via the inductive coil for a first time period, and to disable the transcutaneous transfer of power from the charger power supply to the implantable power supply via the inductive coil for a second time period.

18. The implantable medical system of claim 17, wherein the implantable power supply is part of an implantable component and the wireless charger further comprises a sound processor, wherein the circuit is further configured to transcutaneously transfer data from the sound processor to the implantable component via the inductive coil.

19. The implantable medical system of claim 17, wherein the circuit comprises a power detector connected to the inductive coil, wherein the power detector is configured to detect the presence of an inductive field generated by the auxiliary charger.

20. The implantable medical system of claim 19, wherein the power detector is configured to periodically determine whether the auxiliary charger is capable of supplying power sufficient to recharge the charger power supply.

21. The implantable medical system of claim 19, wherein in response to detecting the presence of the inductive field generated by the auxiliary charger, the circuit is automatically arranged to route power from the inductive coil to the charger power supply.

22. The implantable medical system of claim 12, wherein the controller is configured to enable the transcutaneous transfer of data from the charger to the implantable component via the inductive coil during the second time period.

23. The implantable medical system of claim 17, wherein the implantable medical system is a cochlear implant system.

24. The implantable medical system of claim 17, wherein the circuit is configured to monitor for the presence of the auxiliary charger during the second time period.

25. The implantable medical system of claim 24, wherein when the circuit detects the presence of the auxiliary charger, the inductive coil is configured to receive power from the auxiliary charger and the circuit is configured to enable the transfer of power received from the auxiliary charger to the charger power supply.

26. The implantable medical system of claim 25, wherein before enabling the transfer of power received from the auxiliary charger to the charger power supply, the circuit is configured to perform a check to determine if the charger power supply can accept additional power.

27. The implantable medical system of claim 17, wherein the controller is configured to enable the transfer of data via the inductive coil during the second time period.

* * * * *